United States Patent [19]
Aguilera

[11] 3,949,225
[45] Apr. 6, 1976

[54] INFRARED IMAGING APPARATUS

[75] Inventor: Robert A. Aguilera, Pasadena, Calif.

[73] Assignee: Xerox Corporation, Stamford, Conn.

[22] Filed: Sept. 23, 1974

[21] Appl. No.: 508,387

[52] U.S. Cl. ................ 250/334; 250/330; 250/332
[51] Int. Cl.² ........................................ H01J 31/50
[58] Field of Search..................... 250/330, 332, 334

[56] References Cited
UNITED STATES PATENTS

| | | | |
|---|---|---|---|
| 3,562,529 | 2/1971 | Engborg et al. ..................... | 250/334 |
| 3,699,341 | 10/1972 | Quillinan et al. ................ | 250/330 X |
| 3,728,545 | 4/1973 | Abel .................................. | 250/334 |
| 3,781,559 | 12/1973 | Cooper et al. ..................... | 250/334 |

*Primary Examiner*—Archie R. Borchelt
*Attorney, Agent, or Firm*—John E. Beck; Terry J. Anderson; Irving Keschner

[57] ABSTRACT

Infrared radiation over a field of view is scanned in a first direction by an azimuth scan mirror and optically coupled to a spherical reflecting mirror. The scanned infrared radiation is reflected by the spherical mirror to a first surface of a vertical scanning mirror which forms an image on an adjacent detector array. The electrical signal output of the detector array, proportional to the intensity of the detected infrared radiation, is processed and coupled to an array of light emitting elements. The array of light emitting elements produces a visible image, corresponding to the infrared image, which is projected onto the other surface of the vertical scanning mirror, the visible radiation reflected therefrom being optically coupled to the rear surface of the azimuth scan mirror and thereafter to a recording medium or display device to produce a thermal image of the field of view. The light emitting elements in the array are arranged in a manner whereby the final imagery produced is essentially free of raster lines.

18 Claims, 6 Drawing Figures

INFRARED IMAGING APPARATUS

The invention herein described was made under a contract with the Department of the Army, Mobility Equipment Research and Development Center, Fort Belvoir, Va. Contract No. DAAK02-73-C-0399.

BACKGROUND OF THE INVENTION

Imaging systems for converting infrared radiation, invisible to the unaided human eye, to visible radiation have found wide applications. For example, infrared sensors have been utilized as intrusion detectors wherein it is desired to identify an intruder in a secure area without requiring active illumination; for medical diagnosis such as in mammography; and other applications as described, for example, in U.S. Pat. No. 2,895,049.

Prior art infrared imaging systems, such as that disclosed in the aforementioned patent and U.S. Pat. No. 3,509,345, generally incorporate an infrared detector which is caused to optically scan over the field of view, producing electrical signals in accordance with the detected infrared radiation. The electrical signals from the detector are processed and applied to a light generating means which generates a visible image corresponding to the detected infrared radiation. The generated visible image may be recorded (or displayed) by scanning the visible image in synchronism with the detected infrared image and focusing the visible image on the light sensitive surface of a film, for example.

The infrared imaging device described in the aforementioned patents utilize a single, double-sided two axis scanning mirror to both scan the infrared field of view and to record the corresponding visible image on a recording medium. Although scanning of the field of view and the recording medium are accomplished simultaneously, eliminating synchronization problems, the use of a single double-sided scanning mirror limits both the speed of scan and the field of view which can be covered by the scanner. In particular, if full-field coverage is required by the $x$-direction and $y$-direction scanning mirror, the single mirror must be gimballed in both the $x$-direction and the $y$-direction, the drive mechanism for the inner gimbal automatically becomming part of the load which must be driven by the outer gimbal drive. The scanner drive mechanisms required to provide full field coverage are either galvanometers or dc torque motors and, in either case, the mass of these devices will add to the inner gimbal a load many times the mirror mass. Thus, this combined driver/mirror mass on the inner gimbal will considerably increase the inertia which must be driven by the outer gimbal drive mechanism (outside gimbal). This increased mass will greatly reduce the attainable scan rate on the outside gimbal, in addition to the increased power which will be required to drive it. Further, many of the prior art systems which utilize a single double-sided scanning mirror (with detectors and light emitters) use principally a linear array of equally spaced infrared detectors which are placed over the entire image height of the system. With the detector array placed over the full height of the field of view (FOV), the $y$-direction motion requirement is reduced to the very small motion required to scan the distance between detectors (interlace) as opposed to scanning the entire $y$-direction FOV. Although the required $y$-direction motion is less, a possible disadvantage with the aforementioned detector arrangement makes its used less attractive. In particular, when a channel (portion of system which electrically processes the output signal from an infrared detector element) becomes disabled or the channel gain varies, light or dark raster line or lines will appear in the output imagery, reducing the resolution and information content thereof.

SUMMARY OF THE PRESENT INVENTION

The present invention provides an infrared radiation scanner and display device wherein incoming infrared radiation in the field of view of the device is detected and converted to a corresponding visible image which may be recorded or displayed.

In particular, the incoming infrared radiation is scanned in a first direction by an azimuth scan mirror and optically coupled to a spherical reflecting mirror. The scanned infrared radiation is reflected by the surface of a vertical scanning mirror which forms an image on an adjacent detector array. The electrical signal output of the detector array, proportional to the intensity of the detected infrared radiation, is processed and coupled to an array of light emitting elements. The array of light emitting elements produces a visible image, corresponding to the infrared image, which is projected onto the other surface of the vertical scanning mirror, the visible radiation reflected therefrom being optically coupled to the rear surface of the azimuth scan mirror and thereafter to a recording medium or display device producing a thermal image of the field of view. The light emitting elements in the array are arranged in a manner whereby the final imagery produced is essentially free of raster lines.

It is the object of the present invention to provide apparatus for converting infrared radiation in the field of view of the apparatus to a corresponding visible image.

It is a further object of the present invention to provide apparatus for scanning an infrared radiation detector array over a field of view and modifying the light output of light emitting means in accordance therewith to produce a corresponding visible image which may be recorded or displayed.

It is a further object of the present invention to provide apparatus for scanning an infrared detector array over a field of view and modifying the light output of light emitting means in accordance therewith to produce a corresponding visible image, said apparatus incorporating two independent scanning mirrors, the first, or aximuth scanning mirror, scanning the field of view in the $x$-direction and the second, or elevation scanning mirror, scanning the field of view in the $y$-direction.

It is still a further object of the present invention to provide apparatus for scanning the infrared field of view of the apparatus in first and second direction and converting the scanned image to a corresponding visible image, said apparatus incorporating two independent scanning mirrors whereby increased scanning rates and an increased scanner field of view in both the $x$ and $y$-directions are provided.

It is a further object of the present invention to provide apparatus for scanning an infrared detector array over a field of view and modifying the light output of light emitting means in accordance therewith to produce a corresponding visible image, said apparatus incorporating two independent scanning mirrors, said light emitting elements being arranged in a manner whereby the final imagery is essentially free of raster

DESCRIPTION OF THE DRAWINGS

For a better understanding of the invention, as well as other objects and features thereof, reference is made to the following description which is to be read in conjunction with the accompanying drawing wherein.

DESCRIPTION OF THE PREFERRED EMBODIMENT

Figure 1:
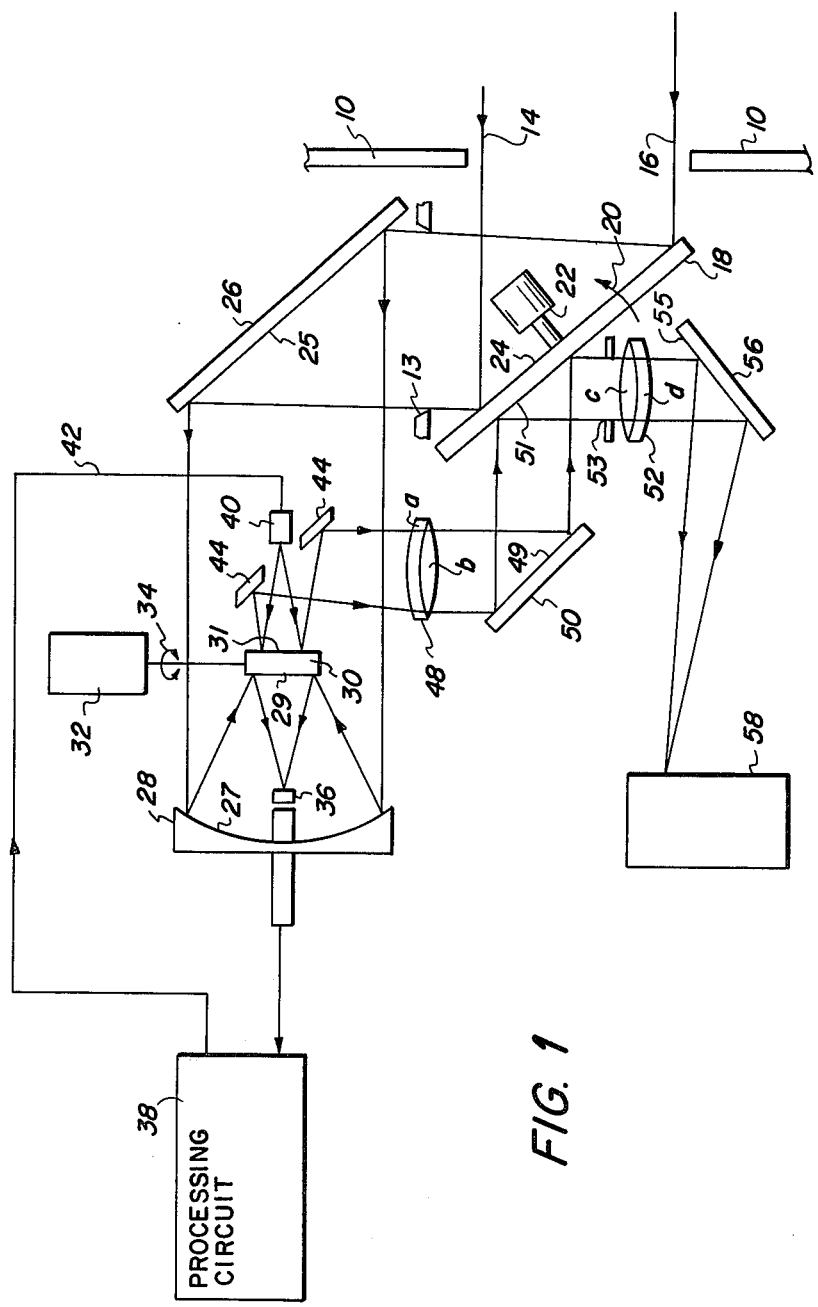
FIG. 1 is the schematic diagram of the infrared imaging device of the present invention.

Referring now to FIG. 1, the infrared imaging apparatus of the present invention is illustrated. In particular, stop member 10 defines an entrance aperture 12 through which infrared, or thermal, radiation in the field of view of the apparatus is received. The infrared radiation may, for example, be emitted by an object, animate or inanimate, located at a location remote from the imaging apparatus. The detected infrared radiation (having a wavelength in the range of 3 to 5 microns) is indicated symbolically by rays 14 and 16 and is incident upon a first surface of scanning mirror 18. As will be described in more detail hereinafter, mirror 18 is caused to rotate in the direction of arrow 20 (the azimuth, or x-direction) by scan drive mechanism 22 (such as a galvanometer). The incident infrared radiation is reflected from surface 24 of scanning mirror 18 and passes through aperture stop 13 onto surface 25 of mirror 26, mirror 26 reflecting, or folding, the incident infrared energy to surface 27 of spherical infrared mirror 28. Surface 27 of spherical mirror 28 reflects the infrared energy incident thereon to surface 29 of scanning mirror 30. Scanning mirror 30 is driven by scan drive mechanism 22 (such as a galvanometer) which causes the scan mirror 30 to rotate in the direction (the elevation, or y-direction) shown by arrow 34. The circuitry utilized to linearly drive mirrors 18 and 30 has not been shown since standard techniques are utilized.

The incident infrared energy is reflected from surface 29 of scan mirror 30 onto infrared detector array 36 mounted at the center of mirror 28. The detector array 36 comprises a matrix of semiconductor elements which generate an electrical output proportional to the intensity of the infrared energy incident upon the element. In the preferred embodiment, the detector array 36 comprises PbSe photoconducting elements. The electrical signal which is generated by detector array 36 is coupled to processing circuit 38 via lead 39, wherein the signals are amplified and processed. The signal output from processing circuit 38 is coupled to a matrix of light emitting elements 40, via lead 42. In a preferred embodiment, the matrix of light emitting elements 40 comprise light emitting diodes (LED's), the diode material in the preferred embodiment comprising GaAsP. The array of light emitting elements 40 are configured in a geometrical pattern similar to the array of elements in detector 36. A one to one correspondence must exist between the detector matrix array 36 and the array of light emitting elements 40. This does not require that their physical sizes need be identical but rather that the number of elements and general arrangement of the elements in each array must be the same. Therefore, for a 2 by 5 array of 10 detector elements, a light emitting element array of 2 by 5 with 10 elements should be used. This correspondence is necessary so that the location of the infrared radiation detected on one or more detectors will be accurately transposed to the corresponding light emitting elements in array 40.

The light energy from the light emitting array 40, which corresponds to the thermal image of the detected infrared energy, is reflected from surface 31 of elevation scan mirror 30, the reflected energy being folded by mirror 44 (mirror with a clear aperture in its center) to collimator lens 48. The collimated light from lens 48 is reflected from surface 49 of folding mirror 50 and directed to surface 51 of scanning mirror 18. The light energy reflected from surface 51 of scanning mirror 18 is collected by optical element 52 via aperture stop 53 and optically coupled to surface 55 of mirror 56. The visible light energy reflected from mirror surface 55 is focused onto the image plane of recording or display medium 58. If the recording medium 58 comprises film, the focused light beam strikes the light sensitive surface of the film to provide a thermal image of the field of view of the imaging apparatus. Alternately, medium 58 may comprise a vidicon wherein the image can be recorded and then displayed on a cathode ray tube.

Spherical mirror 28 can be made of any number of inexpensive materials, such as aluminum, glass or plastic, the cost of finishing and coating mirror surface 27 being relatively inexpensive. As shown in FIG. 1, collimator 48, in the preferred embodiment, comprises a doublet (a concave-convex element a cemented to a biconvex element b) and collector element 52 comprises a doublet (a biconvex element c cemented to a concave-convex element d).

In operation, scan drive mechanisms 22 and 32 are energized to initiate the scan of the field of view of the imaging apparatus. Since scanning mirrors 18 and 30 are independently driven, higher scanning rates may be attained then would be possible if both motions were to be obtained from a single mirror alone.

The scanning mirrors 18 and 30 provide an X-Y scan of the field of view of the apparatus and radiation reflected therefrom, incident on surface 24 of scanning mirror 18, is reflected to folding mirror 26. Mirror 26 in turn reflects the detected infrared energy to surface 27 of spherical mirror 28 which collects and directs the infrared energy onto surface 29 of scanning mirror 30. Surface 29 reflects the incident infrared energy onto detector 36, where it is focused. The electrical signals on lead 39 generated by detector 36 are amplified and processed in processing circuitry 18. The processed signal, representing the detected infrared image, is then applied to the matrix of light emitting elements 40 which generate visible radiation which corresponds to the detected infrared image. The visible radiation emitted from light emitting elements 40 is incident on surface 31 of scanning mirror 30. Scanning mirror 30 directs the incident visible radiation to folding mirror 44 which reflects the light beam to collimator doublet lens 48. It is to be noted that since both the infrared energy reflected from surface 29 of scanning mirror 30 to the detector array 36 and the visible energy emitted from light emitting array 40 are incident on the same scanning mirror 30, synchronization of the infrared and visible scans in the vertical direction is unnecessary.

The collimated visible radiation is folded by mirror 50 and reflected to surface 51 of scanning mirror 18. Since both the infrared energy reflected by surface 24 of scanning mirror 18 and the visible light reflected by surface 51 of the scanning mirror are incident on the same scanning mirror, synchronization of the infrared and visible scans in the horizontal direction is unnecessary.

The visible radiation reflected from surface 51 of scan mirror 18, collected and focused by doublet lens element 52 via aperture stop 53, is reflected by mirror surface 55 to the image plane at recording medium 58.

In the apparatus described hereinabove, the detector and light emitting arrays 36 and 40, respectively, are not required to be placed across the full field of view of the apparatus as is usually the case where scanning is done only in one direction and provides final imagery which is essentially free of raster lines as will be explained more fully hereinbelow with reference to FIGS. 3, 4 and 5.

In the preferred embodiment of the invention, aperture stop 13 is 4 inches and the radius of curvature and focal length of spherical mirror 28 is twelve inches and 6 inches, respectively, forming an effective $f/1.5$ system. Since scanning takes place in front of aperture stop 13, the infrared energy reaching spherical mirror 27 is stationary in the azimuth, or $x$-direction.

Figure 2:
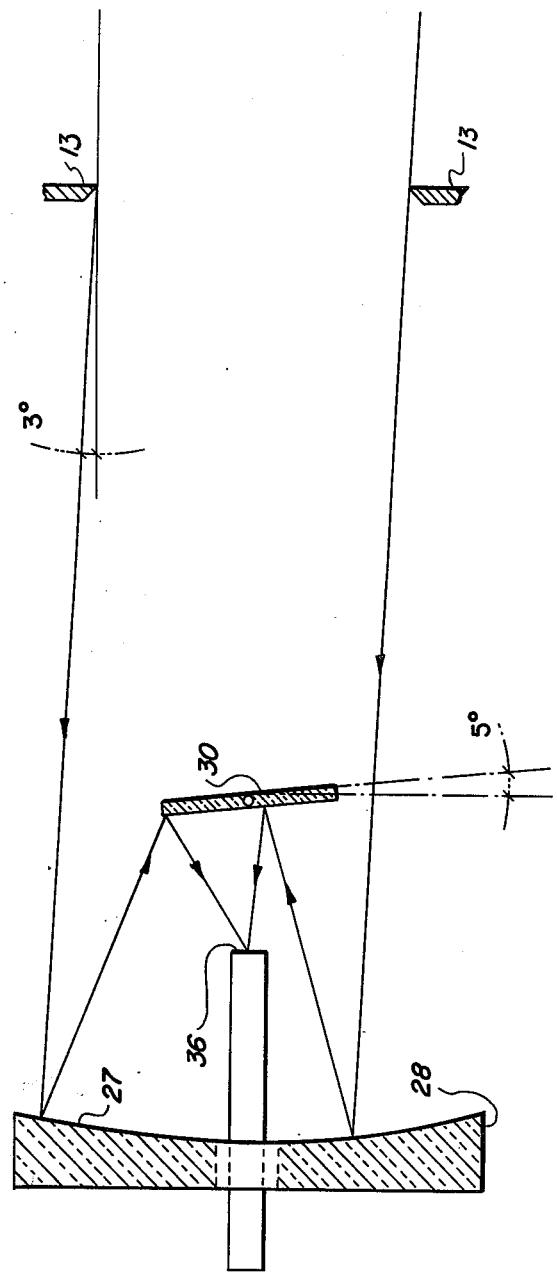
FIG. 2 is an elevation view of optical portions of the device shown in FIG. 1.

FIG. 2 shows the optical system of FIG. 1, in simplified form, in an elevation view. As the elevation scan mirror rotates through a predetermined angle, such as five degrees, only infrared energy coming through the aperture stop 13 within an angle related to the predetermined scan angle (i.e. 3°) in elevation will be focused upon detector array 36. The infrared energy moves in elevation along spherical mirror 28 as scanning takes place.

Figure 3:
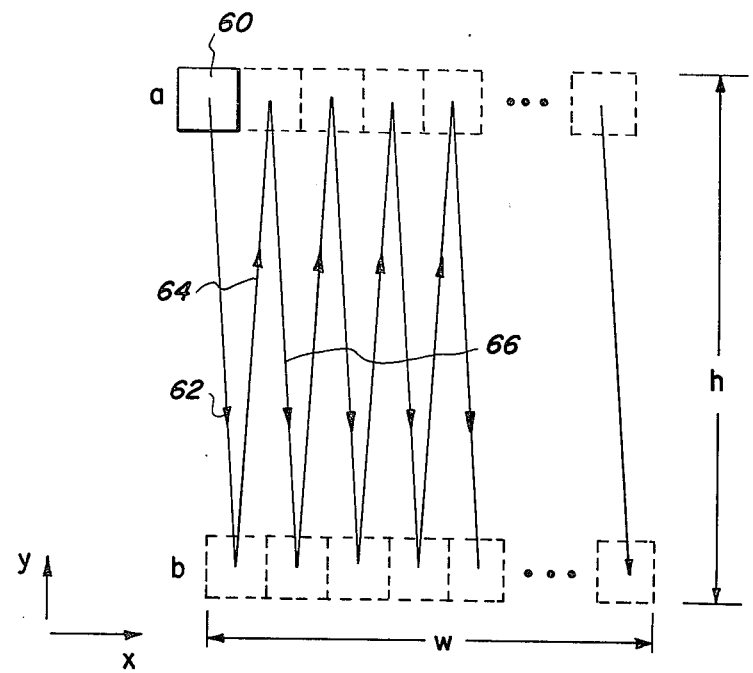
FIG. 3 illustrates the preferred scan pattern for a single light emitting element.

The scan pattern formed at the imaging plane of recording medium 58 by a single light emitting diode 60 is shown in FIG. 3. Although not to scale, the figure illustrates the motion through which the visible radiation generated by diode 60 moves in order to maintain flat imagery (no raster) at the imaging plane of recording medium 58. The "vertical" scan pattern of diode 60 initially traverses the path shown by arrow 62 from position a to position b; returns to position a along the path shown by arrow 64; returns to position b along the path shown by arrow 66; and so on. For illustrative purposes, only five down-scans have been shown. It should be noted, however, that the number of scans in the $x$-direction (or total scan width $w$) is dependent upon the angular displacement of scanning mirror 18. The number of scans in the $y$-direction is dependent upon the scan rate of mirror 30 while the scan height $h$ is dependent upon the angular displacement of mirror 30. In a preferred embodiment, $w$ corresponds to mirro 18 being displaced (total field of view) a total of 6° (optical field of view of 12°) while $h$ corresponds to mirror 30 being displaced 10° (optical field of view of 6°).

Figure 4:
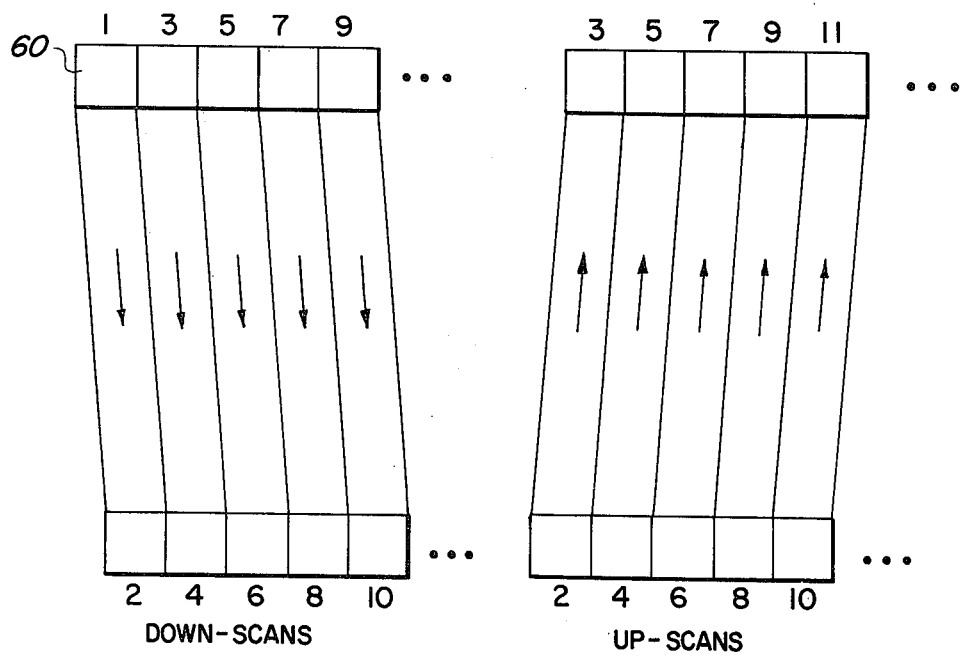
FIG. 4 illustrates the uniformity of imagery generated by the preferred scan pattern for the light emitting array.

To illustrate that the motion shown in FIG. 3 results in flat imagery, reference is made to FIG. 4, which separates the up-scan and down-scan motion of the visible radiation generated by diode 60. Beginning at position 1 at the left hand portion of the figure, the visible radiation will trace a scan line equal to its own width as it moves down to position 2. The next scan line will be an up-scan from position 2 to position 3 shown at the right-hand portion of the figure. The next down-scan from position 3 to position 4 is as shown. Scan lines 1 to 2 and 3 to 4, it should be noted, are together with no space, or raster line, therebetween. Scan lines 2 to 3 and 4 to 5 will similarly be together as will all adjacent down-scan and up-scan lines. Since all the up-scans and down-scans will fill in a complete image, the final imagery, which is the sum of the up-scans and down-scans, will be a flat or raster free, image.

Figure 5A:
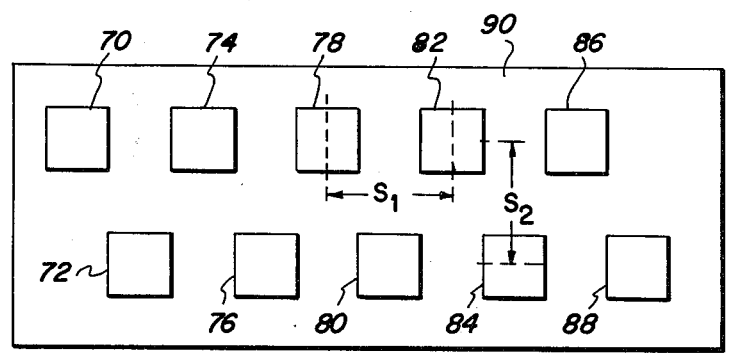
FIG. 5 (a) illustrates the preferred light emitting array configuration and 5(b) illustrates the overscanning patterns generated by the array configuration illustrated in FIG. 5(a).
Figure 5B:
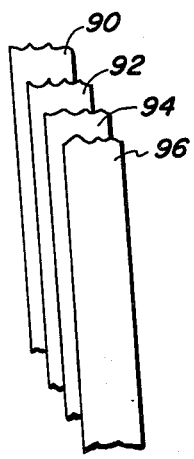

The discussion with regards to FIGS. 3 and 4 is true using a single diode only, but it requires considerable scanning accuracy to maintain perfect alignment between separate scan lines. The scanning accuracy requirement is eased considerably when multiple light emitting diode elements are used. FIG. 5a illustrates the preferred light emitting diode array embodiment. In this embodiment, 10 diode elements 70, 72, 74 . . . 88 are formed on substrate 90 in a conventional manner. The spacing between diode elements is chosen so that if the scan is the same as for the single diode scan described with reference to FIGS. 3 and 4, the sum of the raster lines from all the diode elements 70, 72 . . . 88 will be displaced one from the next by exactly one fourth the width of a single diode. The resultant overlay pattern will be as shown in FIG. 5b, the scan patterns 90, 92, 94, 96 . . . being produced by diode elements 70, 72, 74, 76 . . . The resultant effect of arranging the diodes in this manner will be that of the flatness of the imagery (elimination of raster) will be less sensitive to variations in the scan pattern than if only a single diode element were used. In a typical configuration, each diode was approximately 0.0075 inches by 0.0075 inches, the center-to-center spacing $S_1$ between adjacent diodes in the same row being approximately .015 inches, and the center-to-spacing $S_2$ between diodes in adjacent rows being approximately 0.022 inches. In this configuration, if the diodes 72, 76, 80, 84 and 88 in the second row of the array were displaced vertically and aligned with diodes 70, 74, 78, 82 and 86 in the first row, each of the diodes would be adjacent each other with no (or minimal) spacing therebetween. Although only two rows each with five diode elements are shown, additional rows and diode elements may be utilized to ensure flat imagery.

The elevation scan rate of the system, in the preferred embodiment, is a 100 Hz sinusoid, providing 200 scan lines per second, the azimuth scan mirror 18 preferably being driven in a continuous manner. If the azimuth scan mirror is to be driven in a sinusoid mode, its scanning rate should be less than the elevation scan rate in order to avoid raster lines. If it is desired, for example, to produce an image in 1 second, each diode provides 200 scan lines (a total of 2000 scan lines for the array) as mirror 18 traverses approximately 12° in aximuth. After scanning mirror completes the azimuth scan, the visible radiation from the light emitting diodes is extinguished and scanning mirrors 18 and 30 are reset to their starting positions by conventional techniques.

In summary, the technique of full-field scanner coverage as described hereinabove provides several advantages over those systems which utilize a detector array along the full height of the field of view. Because each detector/diode combination will independently create a complete image of the scene, the system becomes substantially insensitive to channel-to-channel variations, with a minor effect upon the quality of the imagery produced. Further, since scanning for each direction becomes entirely independent of one another in accordance with the teachings of the present invention, the limitations of the prior art double-sided single scanning mirror described hereinabove is avoided. In particular, although two scan mirrors are required instead of one, the mass that must be driven by each scan drive mechanism becomes the mass of the mirror alone, and not the combination scan drive and mirror mass. Thus reduced power and a higher scan rate will be obtainable in at least one of two scan directions.

While the invention has been described with reference to its preferred embodiment, it will be understood by those skilled in the art that various changes may be made and equivalents may be substituted for elements thereof without departing from the true spirit and scope of the invention. In addition, many modifications may be made to adapt to particular situations or material to the teaching of the invention without departing from its essential teachings.

What is claimed is:

1. Apparatus for producing a light output pattern which corresponds to infrared radiation received from the field of view of the apparatus comprising:
   first scanning means having first and second reflective surfaces, said first scanning means scanning the received infrared radiation incident on said first reflective surface from said field of view in a first direction,
   first means for optically coupling the scanned infrared radiation reflected from the first surface of said first scanning means to second scanning means having first and second reflective surfaces, said second scanning means scanning said field of view in a second direction,
   second means for optically coupling the infrared radiation reflected from the first surface of said second scaning means to an infrared detector array, said infrared detector array producing electrical signals in accordance with the infrared radiation received from the field of view of said apparatus, and
   means for coupling said electrical signals to an array of light emitting elements, the light output pattern therefrom corresponding to said received infrared radiation.

2. The apparatus as defined in claim 1 further including third means for optically coupling the light output from said array of light emitting elements to the second surface of said second scanning means, fourth means for optically coupling the light reflected therefrom to the second surface of said first scanning means, and fifth means for optically coupling the light reflected therefrom to a recording medium or display device whereby a visible image of said received infrared radiation is produced.

3. The apparatus as defined in claim 1 wherein said light emitting elements comprise light emitting diodes.

4. The apparatus as defined in claim 3 wherein said infrared detector array comprises PbSe photoconducting elements.

5. The apparatus as defined in claim 4 wherein said first optically coupling means comprises a spherical reflecting element.

6. The apparatus as defined in claim 2 wherein said recording medium comprises a light sensitive surface and wherein the radiation reflected from the second surface of said first scanning means is incident thereupon to produce a visible image of the field of view of the apparatus.

7. The apparatus as defined in claim 1 wherein said array of light emitting elements are arranged to produce a substantially raster-free image.

8. The apparatus as defined in claim 7 wherein said array of light emitting elements are formed in a plurality of rows, a light emitting element in one row being aligned between two adjacent light emitting elements in an adjacent row.

9. Apparatus for producing a light output pattern which corresponds to infrared radiation received from the field of view of the apparatus comprising:
   first scanning means having first and second reflective surfaces, said first scanning means scanning the received infrared radiation incident on said first reflective surface from said field of view in a first direction,
   first means for optically coupling the scanned infrared radiation reflected from the first surface of said first scanning means to second scanning means having first and second reflective surfaces, said second scanning means scanning said field of view in a second direction,
   second means for optically coupling the infrared radiation reflected from the first of said second scanning means to an infrared detector array, said infrared detector array producing electrical signals in accordance with the infrared radiation received from the field of view of said apparatus, and
   means for coupling said electrical signals to an array of light emitting elements, said array of light emitting elements being formed in an array comprising a plurality of rows and columns, alternating rows in said array having light emitting elements in every other column, the rows adjacent said alternating rows having light emitting elements in columns in which the adjacent alternating rows do not contain light emitting elements whereby a substantially raster-free light output pattern, corresponding to said received infrared radiation, is formed.

10. The apparatus as defined in claim 9 wherein each light emitting element generates a scan line in the image, the scan lines generated by a light emitting element in an alternating row and an adjacent light emitting element in the adjacent row overlapping.

11. The apparatus as defined in claim 10 wherein said first scanning means scans at a first predetermined rate and said second scanning means scans at a second predetermined rate, said second predetermined rate being greater than said first predetermined rate.

12. The apparatus as defined in claim 9 further including third means for optically coupling the light output from said array of light emitting elements to the second surface of said second scanning means, fourth means for optically coupling the light reflected therefrom to the second surface of said first scanning means, and fifth means for optically coupling the light reflected therefrom to a recording medium or display device whereby a visible image of said received infrared radiation is produced.

13. The apparatus as defined in claim 9 wherein said light emitting elements comprise light emitting diodes.

14. The apparatus as defined in claim 13 wherein said infrared detector array comprises PbSe photoconducting elements.

15. The apparatus as defined in claim 14 wherein said first optically coupling means comprises a spherical reflecting element.

16. The apparatus as defined in claim 12 wherein said recording medium comprises a light sensitive surface and wherein the radiation reflected from the second surface of said first scanning means is incident thereupon to produce a visible image of the field of view of the apparatus.

17. The apparatus as defined in claim 8 wherein said infrared detector array comprises a plurality of elements formed in a plurality of rows, a detector element in one row being aligned between two adjacent detector elements in an adjacent row.

18. The apparatus as defined in claim 9 wherein said infrared detector array comprises a plurality of elements formed in an array comprising a plurality of rows and column, alternating rows in said array having detector elements in every other column, the rows adjacent said alternating rows having detector elements in columns in which the adjacent alternating rows do not contain detector elements.

* * * * *